United States Patent

Srougi et al.

[11] Patent Number: 5,888,188
[45] Date of Patent: Mar. 30, 1999

[54] MECHANICAL SPHINCTER FOR CONTROLLING URINARY INCONTINENCE

[75] Inventors: Miguel Srougi; Oswaldo Javier Palacios, both of São Paulo, Brazil

[73] Assignee: Fundacao E. J. Zerbini, Sao Paulo, Brazil

[21] Appl. No.: 793,471
[22] PCT Filed: Jun. 7, 1996
[86] PCT No.: PCT/BR96/00024
  § 371 Date: Feb. 14, 1997
  § 102(e) Date: Feb. 14, 1997
[87] PCT Pub. No.: WO97/01309
  PCT Pub. Date: Jan. 16, 1997
[51] Int. Cl.$^6$ .................................................. A61F 2/02
[52] U.S. Cl. .................. 600/30; 600/29; 128/DIG. 25
[58] Field of Search ........................... 600/29, 30, 41; 128/95.1, DIG. 25, 885, 864, 842; 604/346, 347

[56] References Cited

U.S. PATENT DOCUMENTS 3,926,184  12/1975  Gehl.
4,881,939  11/1989  Newman ........................ 128/DIG. 25
5,618,302  4/1997  Martin ........................... 128/DIG. 25

OTHER PUBLICATIONS

Timm, Gerald W. et al, Intermittent Occlusion System, IEEE Transactions on Bio–Medical Engineering, Oct. 1970.

*Primary Examiner*—John P. Lacyk
*Assistant Examiner*—Rosiland Kearney
*Attorney, Agent, or Firm*—Darby & Darby

[57] ABSTRACT

A mechanical sphincter device is to be located in the body for engaging the urethra to control urinary incontinence. The device is formed by a curved piece of flexible material having free ends and a pair of juxtaposed strips of flexible material having their ends connected to the corresponding ends of the curved piece with the urethra disposed between opposing faces of the strips. When the curved piece is in a relaxed state it tensions the strips to apply pressure to the urethra therebetween to restrict flow of urine and when force is applied to the curved piece relaxing the tension on said pair of strips the pressure on the urethra is reduced and permits urine flow.

9 Claims, 1 Drawing Sheet

MECHANICAL SPHINCTER FOR CONTROLLING URINARY INCONTINENCE

FIELD AND BACKGROUND OF THE INVENTION

As it is well known by those skilled in the medical field, urinary incontinence is a serious urological problem, consisting in the incapacity of the individual to retain the urine, frequently causing the involuntary emission thereof.

Urinary incontinence may result from several factors (congenital diseases, acquired diseases, consequences from surgery, etc.). Among the most frequent causes, the following can be mentioned: prostatectomy (partial or total removal of the prostate); epispadias (congenital malformation in which the urethra opens before the end of the penis; injuries in the spinal medulla; fracture of the pelvis; neurogenic bladder, etc.

Undoubtfully, urinary incontinence causes significant impacts in the patient's quality of life, since the involuntary emission of urine is a discomfort, resulting in hygienic and social problems, provoking the reclusion of the patient, impairing his social and professional activities and very often his sexual performance.

Moreover, this disturbance usually brings emotional problems to the patient, who becomes depressed and stigmatized.

Many studies involving several age groups revealed the prevalence from about 17 to 41% of urinary incontinence in the whole population of the planet, consisting therefore in a public health problem. In the United States, for instance, more than 10 billion dollars are used yearly for the treatment of urinary incontinence, this value surpassing those values directed for the treatment of other diseases, such as revascularization of the myocardium or dialysis.

Thus, it can be stated that urinary incontinence is a medical, social and epidemiological problem with very important economic effects.

For all these reasons, urinary incontinence is one of the problems that have been widely studied by many researchers, who are often frustrated for not reaching solutions which are both technically and economically adequate for the problem. Such disease has also caused disappointment in many surgeons, when said symptom arises as a sequella of surgical procedures.

Many have been the methods used for treating urinary incontinence, among which the following can be mentioned: expectant therapy, pharmacological treatment, electronic devices, several surgical procedures and, finally, artificial sphincters. Such methods have been employed in different circumstances and their results have received praises in some instances, but severe criticisms in others.

Many types of prosthesis have already been provided to treat urinary incontinence, such as those from Foley (1947), Berry (1961), Kauffman (1973), Scott (1974) and Rosen (1976), besides Cunhinham's tweezers. All these models were constructed with the aim of causing urethral compression. According to this basic principle, the mechanical compression systems were developed, until the artificial sphincters with self-regulating pressure were provided, such as the various models manufactured by American Medical Systems.

The most modern system used nowadays is the AMS 800, also produced by the above cited company and commercialized since 1983. This model of sphincter comprises an inflatable sleeve, which is implanted in the patient around his urethral canal and connected with a pump, which comprises a valve, a rechargeable delay resistor and a pressure deactivating button. Said pump is also connected with a pressure regulating sump in the form of a balloon.

This artificial sphincter is kept constantly activated, i.e., the sleeve surrounding the urethra is kept permanently inflated, at a predetermined pressure controlled by the sump, thus pressing the urethral canal and avoiding the passage of urine. Only when the patient presses the pressure deactivating button is that said sleeve is deflated, thereby not pressing the urethral canal anymore and, from that time on, allowing the urine to pass. The emission of urine is thus controlled by the patient with urinary incontinence.

One of the inconveniences of this current model of artificial sphincter is the large number of complex connections, which are difficult to handle and increase the risk of mechanical dysfunctions. Another inconvenience resides in its implantation method, which requires a very laborious and complicated surgery, with many details to be strictly followed in order to avoid harmful intercourses, such as infections and erosions.

Another problem of this type of sphincter relates to the installation thereof, which requires skills, for example, to mount the system, to determine the adequate pressure to obtain the continence, to know exactly which details should be avoided so as not to result in the complications cited above and how to treat said complications when they arise.

Finally, a very relevant aspect which limits the application of said artificial sphincter in everyday practice is its cost. Unfortunately, this device is not accessible to all persons, since its value cannot be paid by many patients. On the other hand, this high cost also imposes limitations to the physician, who sees this type of therapeutics as the only possible way of treatment.

DISCLOSURE OF THE INVENTION

With the aim to solve all these inconveniences and to achieve an adequate and objective option to correct and overcome all limitations of the known devices currently used, there has been provided a mechanical sphincter for controlling urinary incontinence and its implantation method. This sphincter consists of a substantially simple device, which is based on totally appliable physical principles, which can be easily installed and which is manufactured in known biocompatible materials. Above all, it is a much more accessible option, on the economical point of view, to a large number of patients, thus representing a very important technological advance in this medical area.

The mechanical sphincter of the present invention consists of a semi-annular piece, which is made from any biocompatible material presenting a spring effect, such as nylon, polyester, steel, etc., and in whose free ends are affixed two strips or screens, parallely disposed to each other and made from any porous and anti-adherent biocompatible material, such as nylon.

Said piece is implanted in the patient's urethra, just behind the scrotal region, said strips or screens being disposed surrounding said urethra and being responsible for producing a urethral closing pressure, in order to guarantee the urinary continence. Said screens are not subjected to shape or tensile alterations upon extending movements, thereby assuring a constant uniform pressure over the urethra. Moreover, since said screens are made from a porous material, they allow the formation of new vessels, which avoid ischemia in the urethra.

The method to implant the mechanical sphincter of the present invention is also much more simpler than the conventional methods. It is only necessary to make a longitudinal trans-scrotal incision by planes, until the urethra is identified and dissected, surrounding it completely. The bed for said screens is prepared and said screens are disposed around the urethra and affixed to the ends of said semi-annular piece with stitches of prolene 0, or any other mechanical fixing means. At this moment, the urethral closing pressure is set by means of a urethral probe connected to an adequate conventional apparatus. Through a transversal abdominal incision, the bladder is identified and a plastic probe is introduced therewithin. Then, physiological serum is infused, till a predetermined intravesical pressure has been reached. The urinary continence is tested after the present mechanical sphincter has been implanted.

Moreover, since the sphincter is implanted very close to the epidermis, the patient may easily find it and, with his fingers, press the ends of the semi-annular piece, one towards the other, in order to release the passage of urine when desired, as explained below.

Thus, after the sphincter has been implanted, the patient will have absolute control over the emission of his urine, since both screens or strips of the device will permanently exert a pressure around the urethra, sufficient to avoid the passage of urine. Only when the patient presses said sphincter, more specifically the free ends of the semi-annular piece, which are permanently tensioned by said screens or strips is that the latter will be loosened, ceasing to press the urethra and consequently allowing the passage of urine. With the mechanical sphincter of the present invention the problem of urinary incontinence is fully solved in a less traumatic form to the patient, since the implantation is achieved in a substantially simpler manner, its utilization is very easy and practical and its cost is substantially lower than that of the conventional devices.

BRIEF DESCRIPTION OF THE DRAWINGS

For illustrative purposes, the present invention will be described below, with reference to the attached drawings, in which.

BEST MODE FOR CARRYING OUT THE INVENTION

The objective of the present invention is to provide a mechanical sphincter for controlling urinary incontinence and its implantation method, said sphincter (1) comprising a semi-annular piece (2) made from any biocompatible material with a spring effect, such as nylon, polyester, steel, etc., in whose free ends are affixed two strips or screens (3), parallely disposed to each other and made from any porous and anti-adherent biocompatible material, such as nylon.

Said sphincter (1) is implanted in the patient's urethra (u), just behind the scrotal region, said strips or screens (3) being disposed surrounding said urethra and being responsible for producing a urethral closing pressure, in order to guarantee the urinary continence.

The method to implant the mechanical sphincter (1) of the present invention consists of making a longitudinal trans-scrotal incision by planes, until the urethra (u) is identified and dissected, surrounding it completely. The bed for the screens (3) is prepared and said screens are disposed around the urethra and affixed to the ends of said semi-annular piece (2) with stitches of prolene 0, or any other mechanical fixing means. At this moment, the urethral closing pressure is set by means of a urethral probe connected to an adequate conventional apparatus. Through a transversal abdominal incision, the bladder is identified and a plastic probe is introduced therewithin. Then, physiological serum is infused, till a predetermined intravesical pressure has been reached. The urinary continence is tested after the present mechanical sphincter has been implanted.

Figure 1:
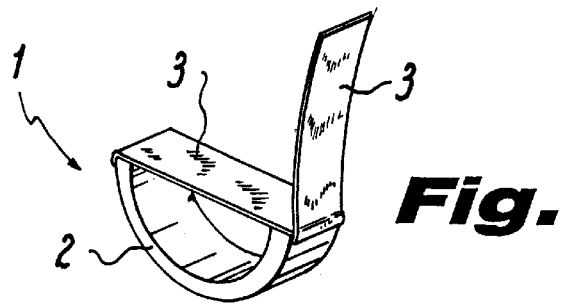
FIG. 1 is a perspective view of the mechanical sphincter of the present invention.
Figure 2:
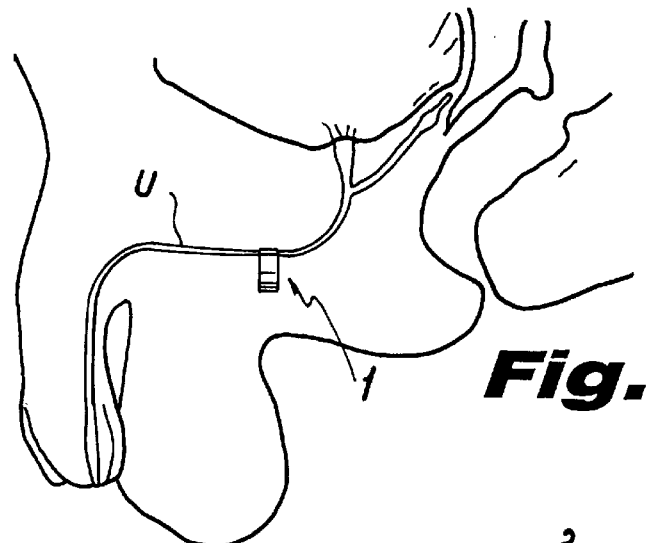
FIG. 2 is a schematic sectional view of the urethral canal of a patient, showing the implantation site of said sphincter.
Figure 3:
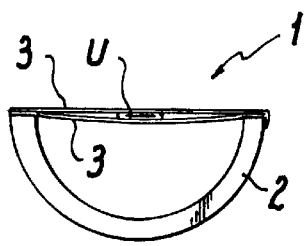
FIG. 3 is a front view of the sphincter of the present invention in a resting position, in which the semiannular piece maintains both screens constantly tensioned, thus pressing therebetween the patient's urethra and avoiding the passage of urine.

Thus, after said sphincter (1) has been implanted, the patient will have absolute control over the emission of his urine, since both screens or strips (3) of the device will permanently exert a pressure around the urethra (u) disposed therebetween, said pressure being sufficient to avoid the passage of urine (see FIG. 3).

Figure 4:
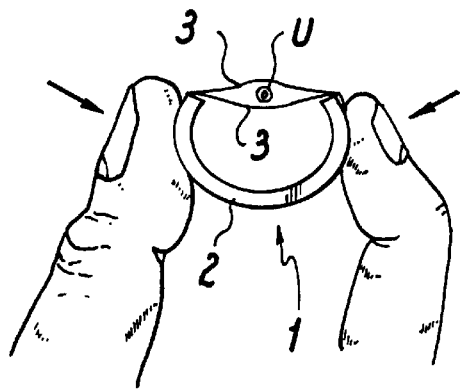
FIG. 4 is the same front view, but now during the pressure exerted by the patient on the semi-annular piece, more precisely at the ends thereof, which are pressed one towards the other, whereby the screens are loosened, ceasing to exert pressure around the urethra and allowing the urine to pass.
Figure 3A:
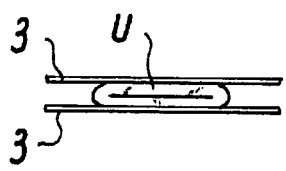
Figure 4A:
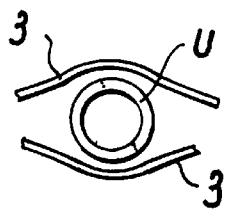

Only when the patient presses said sphincter (1), more specifically the free ends of the semi-annular piece (2), which are permanently tensioned by said screens or strips (3), is that the latter will be loosened, ceasing to press the urethra and consequently allowing the passage of urine (see FIG. 4).

We claim:

1. A mechanical sphincter for controlling urinary incontinence, comprising:

a flexible curved piece of resilient material to be located behind the scrotal region so as to be manually and externally pressible, said curved piece having a pair of ends defining an open section and being deformable by the application of force to bring said ends closer together, and a pair of strips, one end of each of said pair of strips connected to one of the ends of said curved piece, and the other end of each of said pair of strips connected to the other end of said curved piece, with said strips being disposed in opposing relationship one above the other when said strips are tensioned in a relaxed state of said resilient curved piece, and between which the urethra is to be disposed so as to remain under pressure, the tension of said strips being removed and the strips separating when the ends of said curved piece are brought closer together by manually deforming said curved piece to remove pressure on the urethra.

2. A mechanical sphincter as in claim 1 wherein at least one end of one said strip is adhesively connected to a respective end of said curved piece.

3. A mechanical sphincter as in claim 1 wherein the material of said strips is porous and non-adherent.

4. A mechanical sphincter as in claim 1 wherein the material of said strips is a screen.

5. A mechanical sphincter as in claim 1 wherein said curved piece is of semi-circular shape.

6. A sphincter to be located in the body for engaging the urethra to control urinary incontinence comprising:

a curved piece of resilient material having a pair of spaced apart ends; and a pair of strips of flexible material, each of said strips having two ends with one of the ends connected to one end of said curved piece and the other ends connected to the other end of said curved piece with said pair of strips juxtaposed one above the other between said ends of said curved piece, the urethra to be disposed between opposing faces of said strips, said curved piece in a relaxed state tensioning said strips to apply pressure to the urethra therebetween to restrict flow of urine and force applied to said curved piece relaxing the tension on said pair of strips to reduce the pressure on the urethra and permit urine flow.

7. A mechanical sphincter as in claim 6 wherein at least one end of one of said strips is adhesively connected to a respective end of said curved piece.

8. A mechanical sphincter as in claim 6 wherein the material of said strips is porous and non-adherent.

9. A mechanical sphincter as in claim 6 wherein the material of said strips is a screen.

* * * * *

UNITED STATES PATENT AND TRADEMARK OFFICE
CERTIFICATE OF CORRECTION

PATENT NO. : 5,888,188
DATED : March 30, 1999
INVENTOR(S) : Michael SROUGI; Oswaldo Javier PALACIOS It is certified that error appears in the above-identified patent and that said Letters Patent is hereby corrected as shown below:

On the title page, item [30] add the following:

June 29, 1995    Brazil    PI 9502990

Signed and Sealed this

Twentieth Day of July, 1999

Attest:

Q. TODD DICKINSON

Attesting Officer

Acting Commissioner of Patents and Trademarks